United States Patent [19]

Steer et al.

[11] Patent Number: 4,496,354
[45] Date of Patent: Jan. 29, 1985

[54] DRAINAGE BAG ASSEMBLY WITH DRIP TRAY

[75] Inventors: Peter L. Steer; John V. Edwards, both of Sussex, England

[73] Assignee: Craig Medical Products Limited, Sussex, England

[21] Appl. No.: 443,812

[22] Filed: Nov. 22, 1982

[30] Foreign Application Priority Data

Nov. 23, 1981 [GB] United Kingdom ............... 8135253

[51] Int. Cl.³ ............................................. A61M 1/00
[52] U.S. Cl. ..................................... 604/322; 206/466
[58] Field of Search ............... 128/760, 767, DIG. 24; 493/83, 213, 217, 932, 933; 141/10, 68, 114, 313–317; 383/119, 120; 206/966, 466; 215/1 C, 526, 461, 494; 248/459, 174; 604/317, 322–326, 133, 134; 312/1

[56] References Cited

U.S. PATENT DOCUMENTS

| | | | |
|---|---|---|---|
| 3,312,221 | 4/1967 | Overment | 128/275 |
| 3,534,738 | 10/1970 | Hock | 604/325 |
| 3,575,170 | 4/1971 | Clark | 128/275 |
| 3,598,150 | 8/1971 | Nolan | 137/625.32 |
| 3,650,272 | 3/1972 | Ericson | 128/275 |
| 3,661,153 | 5/1972 | Polk et al. | 128/275 |
| 3,716,055 | 2/1973 | Schutlze | 128/275 |
| 3,809,086 | 5/1974 | Schachet et al. | 604/133 |
| 3,831,453 | 8/1974 | McWhorter | 128/275 |
| 4,027,842 | 6/1977 | Mittleman | 248/75 |
| 4,051,578 | 10/1977 | Maaschot | 251/4 |
| 4,085,755 | 4/1978 | Burrage | 128/295 |
| 4,126,135 | 11/1978 | Hinman | 128/275 |
| 4,192,295 | 3/1980 | Sherlock | 128/295 |
| 4,254,771 | 3/1981 | Vidal | 604/325 |
| 4,305,404 | 12/1981 | Dunn | 128/767 |

FOREIGN PATENT DOCUMENTS 1011268 11/1965 United Kingdom ............... 604/317

Primary Examiner—C. Fred Rosenbaum
Assistant Examiner—J. L. Kruter
Attorney, Agent, or Firm—Lawrence S. Levinson; Stephen B. Davis

[57] ABSTRACT

A drainage bag having one wall of substantially rigid liquid-impermeable material and a second wall of flexible liquid-impermeable material secured thereto to define a container. The rigid sheet has at least two apertures with an inlet fitting fixed to one and an outlet fitting fixed to the other. The bottom portion of the rigid sheet extends below the lower edge of the flexible wall to provide a drip tray.

6 Claims, 8 Drawing Figures

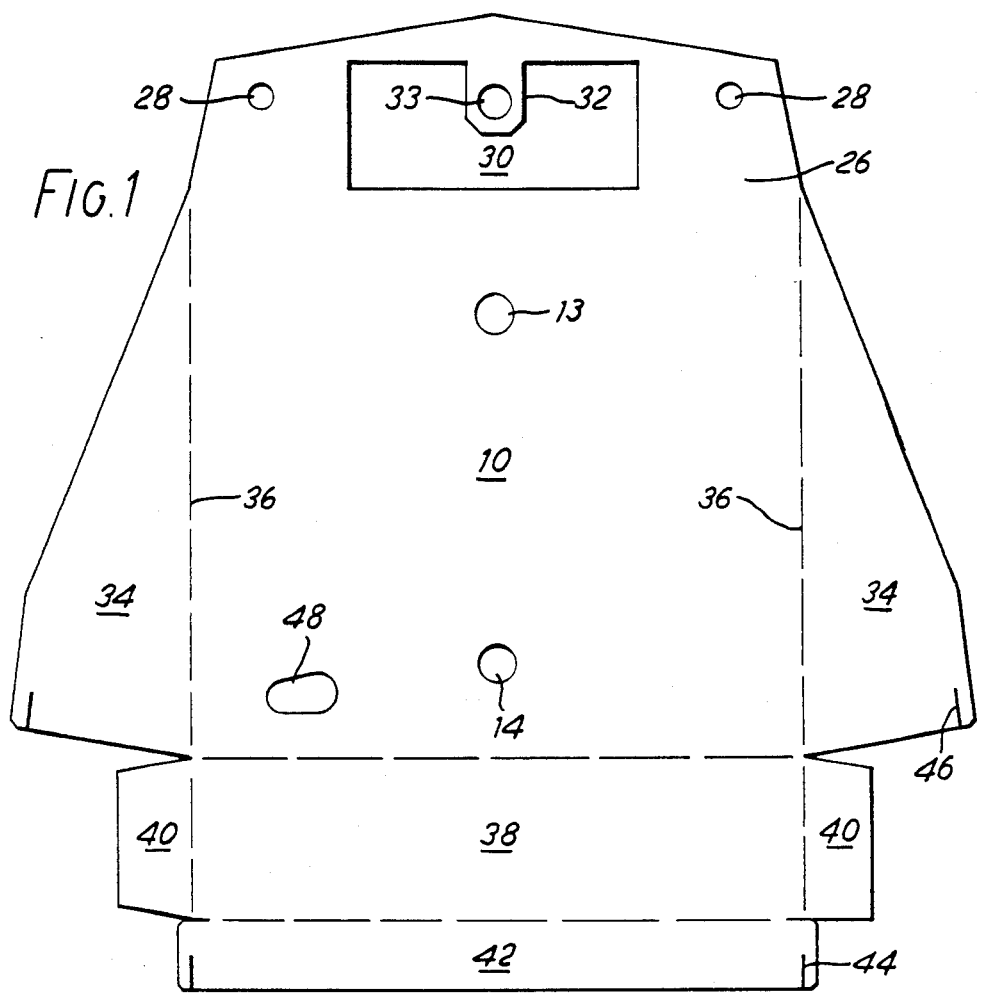

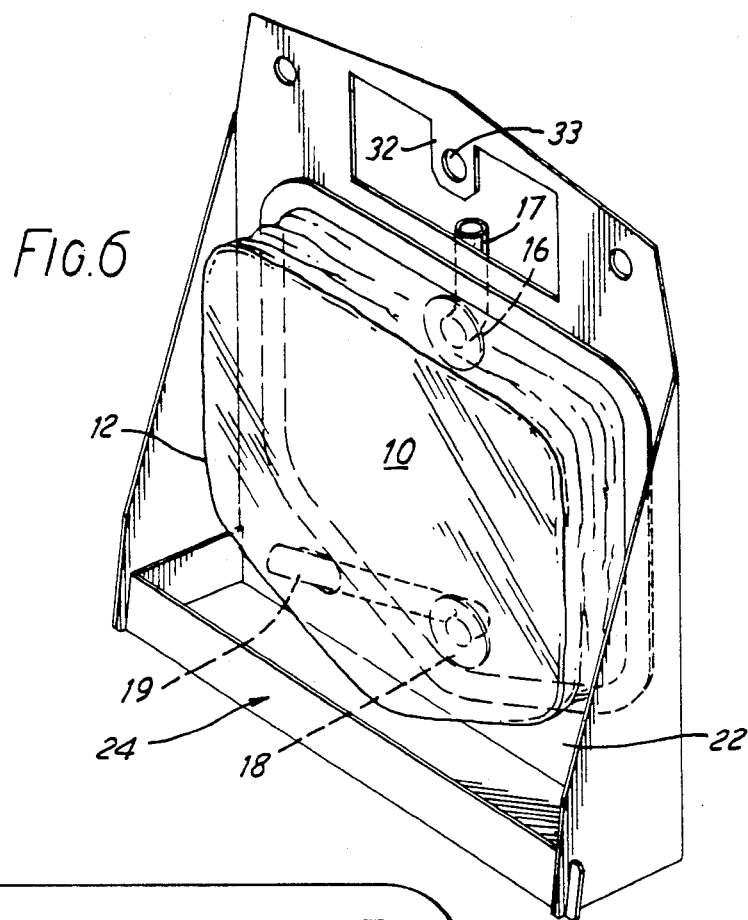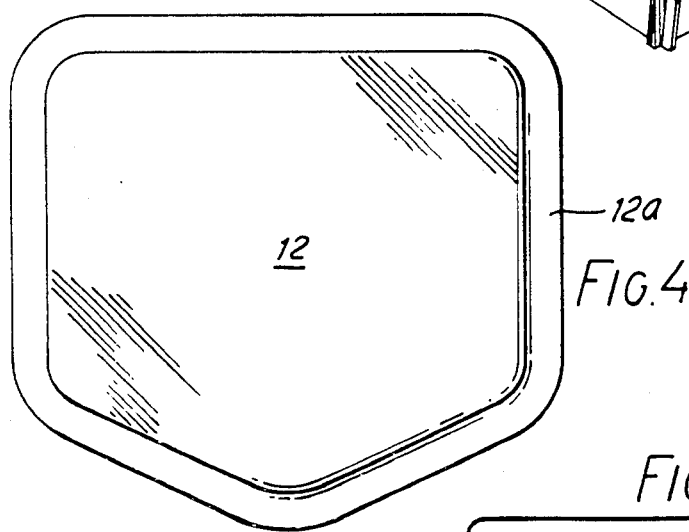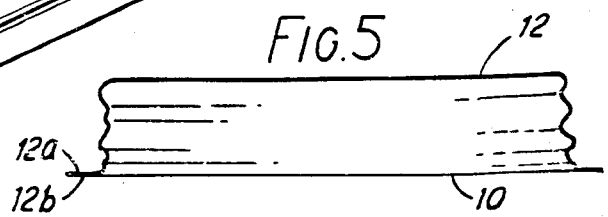

4,496,354

DRAINAGE BAG ASSEMBLY WITH DRIP TRAY

BACKGROUND OF THE INVENTION

This invention relates to a drainage bag such as may be used for the collection of urine from hospital patients or incontinent persons.

Any such bag which is to be re-used must have an inlet, and a chamber or space to receive the liquid and an outlet so that the bag can be emptied at a convenient time and place. Present drainage bags have the liquid-receiving space defined by two superposed sheets of plastics material welded or otherwise secured to each other around their edges. Difficulties arise in securing the inlet and outlet fittings to the superposed sheets and it has not been found possible to do so, up to date, in an entirely satisfactory manner without increasing the number of manufacturing steps and so increasing the complexity and cost of the manufacturing process.

A further disadvantage of most commonly employed urine bags is that they are not self-supporting and so have to be provided with a hanger or other support, or a stand if they are to be placed on a surface such as the floor. Examples of such bags are shown by Polk et al. in U.S. Pat. No. 3,661,153, Schultze in U.S. Pat. No. 3,716,055, Mittleman in U.S. Pat. No. 4,027,842, Maaschot et al. in U.S. Pat. No. 4,051,578 and Sherlock in U.S. Pat. No. 4,192,295. Hinman in U.S. Pat. No. 4,126,135 discloses a self-standing urine bag structure comprising a pair of generally rigid leaves hingedly secured at the apical portions thereof and having a bag suspended therebetween.

SUMMARY OF THE INVENTION

The present invention is a radical departure from the above-described design of drainage bags, and has been made with a view to achieving significant simplification of manufacture and a bag which can support itself.

According to the invention in its broadest aspect, there is provided a drainage bag having one wall of a substantially rigid sheet of liquid-impermeable material and a second wall of flexible liquid-impermeable material secured thereto to define a container, there being at least two apertures in the rigid sheet to one of which is fixed an inlet fitting and to the other of which is fixed an outlet fitting.

In a preferred embodiment of the invention, the rigid sheet is extended below the lower edge of the flexible wall and defines a drip tray. An aperture may be provided above the base of the tray so that the end of an outlet tube can be tucked into the aperture, so ensuring that any drips from the outlet tube fall into the tray.

The rigid sheet may be extended above the upper edge of the flexible wall and may serve as a hanger. For this purpose it may have holes punched in it by which the bag may be suspended from one or more hooks on a stand. The tray beneath the bag, formed by the rigid sheet, extends beneath the bag and constitutes a stable base when the bag is placed on a flat surface.

The rigid sheet which forms one wall of the bag, and which also forms the tray base may for example be of cardboard laminated to one or more liquid-impermeable films. Since urine has corrosive properties, the laminating layer or layers should be suitably chosen.

Also according to the invention, there is provided a method of manufacturing a drainage bag which includes the following steps:

(a) providing at least two apertures in a substantially rigid sheet of material which is to constitute one wall of the bag, (b) securing an inlet and an outlet fitting to the sheet at these apertures, (c) forming or shaping a sheet of flexible material to constitute a second wall of the bag, and (d) securing the periphery of the second wall to the first wall to define a liquid-containing space.

In a preferred embodiment of the invention, the substantially rigid sheet is cropped, in step (a), to provide a blank having such a shape that a lower part of the sheet can be folded up to form a drip-tray, and this folding up operation is carried out after step (d). As an additional (and optional) feature a liquid-absorbent and disinfectant or anti-bacterial substance may be placed or fixed (e.g., adhesively) in the tray so formed.

The second wall may be formed by injection molding of plastics material, or by vacuum-forming, or in any other suitable way. It is advantageous that it be formed in a shape which is to some extent expansible, for example there may be some part of the wall made in a bellows-like configuration. There may be a tab on an upper portion of the substantially rigid sheet to hold and guide a tube leading to the inlet fitting. It will be understood that normally the inlet fitting will be in the upper region of the completed bag and the outlet fitting in the lower, but this may be varied in special circumstances.

BRIEF DESCRIPTION OF THE DRAWINGS

FIG. 1 is a plan view of one form of flat blank from which may be formed the first wall of the bag and the tray therebeneath;

FIG. 2 is a cross-section through one example of a laminate which may be used as the aforesaid substantially rigid sheet;

FIG. 3 shows in cross-section a later step in the manufacture, namely the insertion of the inlet and outlet fittings;

FIG. 4 shows a front view of a vacuum-formed flexible sheet to constitute the second wall of the bag;

FIG. 5 shows diagrammatically in cross-section the uniting of the first and second walls around the periphery of the latter, so defining a liquid-receiving space;

FIG. 6 is a perspective view of one example of bag according to the invention made by the method briefly described above.

DETAILED DESCRIPTION OF THE INVENTION

Figure 7:
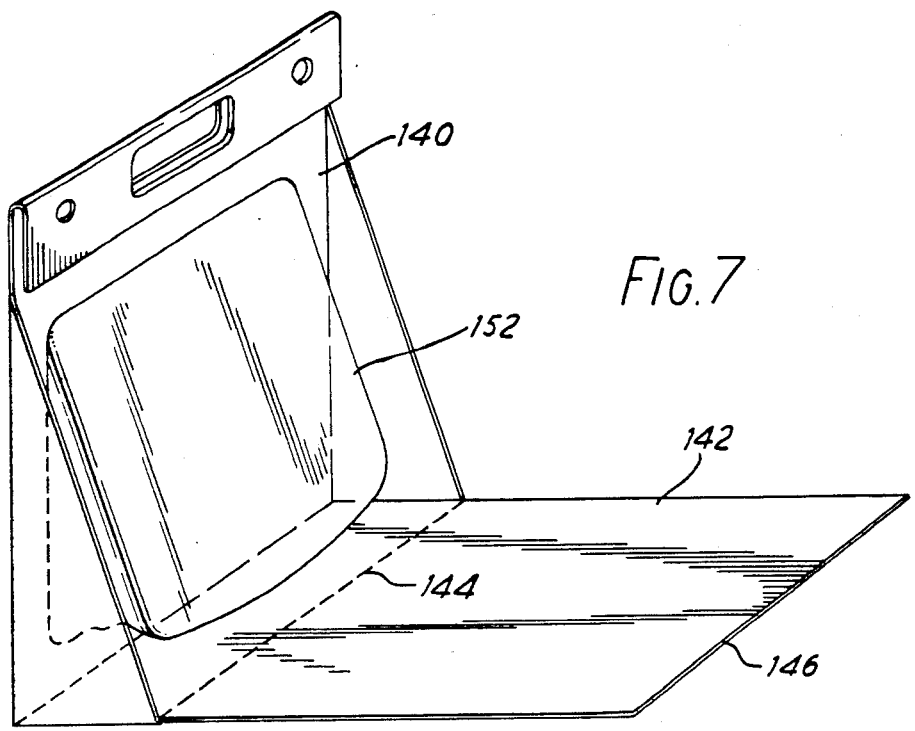
FIG. 7 is a perspective view of a liquid-containing bag in accordance with a further embodiment of the invention.

In this specification, the words "substantially rigid" and "rigid" when applied to the sheet or laminate forming the first wall of the bag are intended to mean rigid in the sense of not deforming or collapsing under forces such as those which would be applied by the weight of urine in the bag when it is full.

The drainage bag illustrated in FIG. 6, and part of which is illustrated in FIG. 1, has one wall 10 of a substantially rigid sheet of liquid-impermeable material and a second wall 12 of flexible liquid-impermeable material secured thereto to define a container. There are two apertures 13, 14 in the rigid sheet 10 to one of which is fixed an inlet fitting 16 (FIGS. 3 and 6) and to the other of which is fixed an outlet fitting 18 (seen only in FIG. 6). As seen in FIG. 6, the rigid sheet 10 is downwardly extended at 22 and when appropriately folded constitutes a drip tray 24.

One suitable form of blank is illustrated in FIG. 1 and is constituted by a central portion having the inlet and outlet apertures 13, 14, an upper portion 26 which serves as a hanger having two circular holes 28 and a rectangular hole 30, there being a fold-over tab 32 having a central hole 33 therein through which can be threaded an inlet tube 17 to be connected in use to the inlet fitting 16. The blank also includes wing portions 34 which (during manufacture or prior to use) may be folded forwardly about fold lines 36, a drip tray portion 38, drip tray sidewall portions 40, and drip tray front wall portion 42. Slots 44 in the drip tray front wall portion 42 engage with slots 46 in the wing portions 34 so that the drainage bag may be assembled in a self-standing manner as illustrated in FIG. 6. A slightly elongated aperture 48 is provided in an area of the blank outside the confines of the container defined by walls 10 and 12. This aperture 48 serves as a retaining hole for a tube 19 which is connected to the outlet fitting 18 and as seen in FIG. 6 this tube 19 extends through the hole 48 to a position where its open end is above the drip tray 38. The base of the drip tray forms a stable support by which the bag may be placed on a horizontal surface, and due to the presence of the wings 34 the stability of the bag is not adversely affected when it is filled with liquid. The top surface of the base of the tray may be covered with a layer of absorbent or germicidal or odor-absorbing material.

As discussed above, an important advantage of the invention is that the bag may be manufactured without difficulties of sealing inlet and outlet fittings between superposed sheets of plastics material, which though not especially difficult of itself, complicates the sequence of manufacturing steps and necessitates a slower and less efficient production method than otherwise could be employed.

According to one embodiment of the present invention, a drainage bag as described above may be made by the following steps. Firstly a blank 10 is cut out according to FIG. 1, from a starting material constituted by a laminate seen in FIG. 2 and having the following layers:

| | |
|---|---|
| Layer 100, polyethylene | 14 gms. per sq. meter |
| Layer 102 cardboard | 290 gms. per sq. meter |
| Layer 104 "SURLYN" or other adhesive layer for laminating aluminum foil to other materials | 18 gms. per sq. meter |
| Layer 106 aluminum foil (standard .009) | 24 gms. per sq. meter |
| Layer 108 "SURLYN" or equivalent | 10 gms. per sq. meter. |
| Layer 110 synthetic plastics layer | 25 gms. per sq. meter. |

Other laminates are equally suitable, and cardboard-based laminates which are corrosion resistant and liquid-impermeable are available on the open market.

At the same time as the blank is punched out and creased, the apertures 30, 33, 13, 14 and 48 are punched therein. Thereafter, inlet and outlet fittings 16, 18 are applied and their flanges are heat welded to the blank 10. In a separate operation, the second wall 12 is formed by vacuum forming, injection molding, or other suitable manufacturing method, from flexible liquid-impermeable material, preferably a heat-weldable synthetic plastics material. This wall is formed in the shape illustrated in FIGS. 4 and 5 and has a marginal edge portion 12a whose surface 12b is then presented to the flat surface of the blank, these two walls are then united by one heat welding operation with no problems of sealing or positioning of inlet and outlet fittings 16, 18. As shown in FIG. 5, it is preferred that part of the second wall 12 should be of concertina or bellows form so that some expansion of internal volume can be achieved.

Thereafter, the wing portions 34 and the drip tray portions are folded into their positions as illustrated in FIG. 6, so producing a stand-alone drainage bag made of relatively inexpensive materials and with a simplified manufacturing procedure.

Advantages of the invention as particularly disclosed and illustrated herein include:

(a) the rigid sheet may be made in one cropping operation;

(b) the flexible wall may be cheaply made by vacuum forming and may be configured (tapered) to lead liquid to the outlet;

(c) the bag is versatile and can be hung up or placed on any relatively flat surface;

(d) the flexible (second) wall may be produced according to a number of different designs, so that the same basic manufacturing process can be used for bags intended for different end uses or different customers; for example (i) an entry chamber could be molded or vacuum formed, into which the inlet fitting would lead directly, or (ii) a conventional flap valve can be readily included, or (iii) an air vent can be included by appropriately shaping and punching a hole in the second wall;

(e) a special connector (e.g., the connector disclosed and claimed in U.S. patent application Ser. No. 336,479), now abandoned in favor of U.S. Pat. Ser. No. 599,132 can be permanently secured to each of the inlet and outlet fittings and in this way the drainage bag becomes part of a modified system which is easily connected to and disconnected from other equipment such as a catheter with consequent saving of nurses time and reduced risk of leakage;

(f) the bag can be transported in flat condition with consequent saving in space; and (g) calibrations can be readily included on the rigid wall so that the bag can be used to measure the volume of urine discharged.

In the foregoing specification, there has been described and illustrated a bag in which the substantially rigid sheet is of a 6-layer laminate. In one alternative embodiment of the invention, to save cost, the sheet may be a two-layer laminate of cardboard and polyethylene. In another alternative embodiment, the substantially rigid sheet may be a 2-layer laminate of cardboard and polyvinyl chloride.

Figure 8:
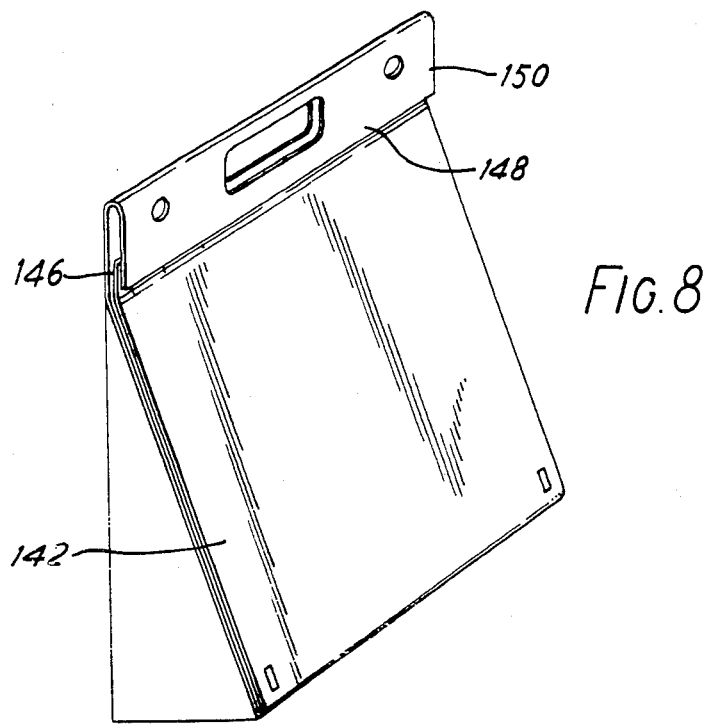
FIG. 8 is a similar view of the bag as shown in FIG. 7, illustrating its flap in a folded-up position.

In yet another embodiment of the invention, illustrated in FIGS. 7 and 8, the rigid sheet has a first portion 140 which is laminated to a plastics material to render it liquid-impermeable and a second portion 142 which is plain cardboard and is connected to the first portion at a fold-line 144. There may but need not be perforations or weakening along the fold line 144 so that the second portion can be torn off if desired, or, if not torn off, can be folded up as indicated in FIG. 8, so that its end 146 is tucked under a suitable flap 148 in the handle portion 150. In this way the contents of the bag, contained within the space defined by the first wall 140 and a second wall 152, are hidden from view.

According to yet a further embodiment of the invention, the wing flaps 34 (FIG. 1) may be joined to the portion 10 by fold lines which are also a line of weakening, so that the flaps 34 can be torn off it is desired to have a simple, light, cheap bag without the stand-up feature.

It will be understood that if minimum initial cost is the aim, the bag can consist merely of the liquid-containing chamber defined by a first liquid-impermeable sheet laminated to a second vacuum-formed liquid impermeable and flexible sheet, there being at least an inlet to the interior formed by an inlet fitting located at or in an aperture in the first sheet.

What is claimed is:

1. A self-supporting closed body drainage bag assembly comprising a first wall formed of a substantially rigid sheet of liquid-impermeable material and a second wall formed of a flexible liquid-impermeable material, said second wall secured to said first wall so as to define a container, said first wall extending beyond the upper and lower edges of said second wall and having wing portions extending beyond the side edges of said second wall, said first wall wing portions being folded forwardly and said first wall extended lower portion being folded and joined to said folded wing portion to form a drip tray means extending beneath said container, said upper extended first wall having at least one hole above said container that serves in use as a hanger, and at least two aperture means forming the inlet and outlet in said first wall for communicating within the confines of the container to one of which is fixed an inlet fitting and to the other of which is fixed an outlet fitting.

2. The drainage bag assembly of claim 1 further comprising an inlet tube connected to said inlet fitting and an outlet tube connected to said outlet fitting, said inlet fitting fixed to an aperture means in the upper region of said container and said outlet fitting fixed to an aperture means in the lower region of said container.

3. The drainage bag assembly of claim 2 further comprising an aperture means in said first wall outside the confines of said container and above said drip tray means so that the end of said outlet tube can be tucked into said aperture means so that any drips from said outlet tube fall into said tray means.

4. The drainage bag assembly of claim 1 wherein said first wall is of cardboard laminated to one or more liquid-impermeable films.

5. The drainage bag assembly of claim 4 wherein said second wall is of vacuum-formed plastic material.

6. The drainage bag assembly of claim 5 wherein part of said second wall is made in bellows-like configuration so that said container can be expanded in internal volume.

* * * * *